US010722404B2

(12) United States Patent
Echeverri et al.

(10) Patent No.: US 10,722,404 B2
(45) Date of Patent: Jul. 28, 2020

(54) COMFORT HEADBAND FOR HEARING PROTECTORS

(71) Applicant: 3M INNOVATIVE PROPERTIES COMPANY, St. Paul, MN (US)

(72) Inventors: Nicolas A. Echeverri, Woodbury, MN (US); Douglas D. Fletcher, Woodbury, MN (US); Oscar M. Hemberg, Dalaro (SE); Eric O. Hemberg, Shatin (HK)

(73) Assignee: 3M Innovative Properties Company, St. Paul, MN (US)

( * ) Notice: Subject to any disclaimer, the term of this patent is extended or adjusted under 35 U.S.C. 154(b) by 436 days.

(21) Appl. No.: 15/548,049

(22) PCT Filed: Jan. 27, 2016

(86) PCT No.: PCT/US2016/015021
§ 371 (c)(1),
(2) Date: Aug. 1, 2017

(87) PCT Pub. No.: WO2016/126469
PCT Pub. Date: Aug. 11, 2016

(65) Prior Publication Data
US 2018/0014973 A1    Jan. 18, 2018

Related U.S. Application Data

(60) Provisional application No. 62/111,532, filed on Feb. 3, 2015.

(51) Int. Cl.
*A61F 11/14* (2006.01)
*H04R 5/033* (2006.01)
*H04R 1/10* (2006.01)

(52) U.S. Cl.
CPC .............. *A61F 11/14* (2013.01); *H04R 1/105* (2013.01); *H04R 1/1008* (2013.01); *H04R 5/0335* (2013.01); *A61F 2011/145* (2013.01)

(58) Field of Classification Search
CPC .... A61F 11/12; A61F 11/14; A61F 2011/145; A61F 2007/005; H04R 1/105;
(Continued)

(56) References Cited

U.S. PATENT DOCUMENTS

| 1,555,928 A | 10/1925 | Morrissey |
| 3,053,944 A * | 9/1962 | Weeks ................. H04R 1/1066 381/377 |

(Continued)

FOREIGN PATENT DOCUMENTS

| CA | 2324534 | 4/2001 |
| CN | 204090087 U | 1/2015 |
| WO | WO 2009/120130 | 10/2009 |

OTHER PUBLICATIONS

"3M Occupational Health & Environmental Safety Division; 3M Peltor Earmuffs—X Series, Optime, Specialty", Peltor Product Brochure, 2012, pp. 1-24.
(Continued)

*Primary Examiner* — Anna K Kinsaul
*Assistant Examiner* — Camtu T Nguyen
(74) *Attorney, Agent, or Firm* — Kevin Weber

(57) ABSTRACT

A hearing protection apparatus is provided. The apparatus comprises a removable compressible pad having a top portion and a bottom portion wherein the compressible pad is configured to be secured to the headband when the apparatus is worn. The compressible pad can provide increased comfort and an improved fit to the user.

18 Claims, 10 Drawing Sheets

(58) Field of Classification Search
CPC ...... H04R 1/1008; H04R 5/0335; H04R 1/10;
A41D 13/15; A41D 13/05
See application file for complete search history.

(56) References Cited

U.S. PATENT DOCUMENTS

| | | | |
|---|---|---|---|
| 3,167,619 A | | 1/1965 | Palmaer |
| D254,183 S | * | 2/1980 | Doodson .................. A61F 5/56 |
| | | | D14/205 |
| 5,574,795 A | | 11/1996 | Seki |
| 5,590,213 A | | 12/1996 | Urella et al. |
| 5,604,813 A | | 2/1997 | Evans |
| 5,819,391 A | * | 10/1998 | Matsushima ...... A44B 18/0003 |
| | | | 24/452 |
| 6,449,806 B1 | * | 9/2002 | Engelhard ............... H04M 1/05 |
| | | | 2/209 |
| 6,724,906 B2 | | 4/2004 | Naksen |
| 7,457,649 B1 | | 11/2008 | Wilson |
| D623,167 S | | 9/2010 | Hildebrandt |
| 8,139,807 B2 | * | 3/2012 | Reiss .................. H04R 1/1083 |
| | | | 381/371 |
| D663,902 S | | 7/2012 | Karlsson et al. |
| D687,409 S | | 8/2013 | Lee et al. |
| 8,767,996 B1 | | 7/2014 | Lin |
| 10,172,742 B2 | * | 1/2019 | Fletcher ............... H04R 1/1083 |
| 2003/0202341 A1 | * | 10/2003 | McClanahan ....... F21V 33/0052 |
| | | | 362/105 |
| 2008/0173313 A1 | * | 7/2008 | Brady ...................... A61F 5/56 |
| | | | 128/848 |
| 2010/0177904 A1 | | 7/2010 | Sung |
| 2011/0019834 A1 | | 1/2011 | Fransson |
| 2013/0047310 A1 | * | 2/2013 | Peebles .................. A61F 9/029 |
| | | | 2/15 |
| 2014/0023222 A1 | | 1/2014 | Ito |
| 2014/0177884 A1 | | 6/2014 | Minarik |
| 2014/0259287 A1 | | 9/2014 | Waters |
| 2014/0348371 A1 | * | 11/2014 | Ishizaki ............... H04R 5/0335 |
| | | | 381/378 |
| 2015/0139472 A1 | | 5/2015 | Solomon |

OTHER PUBLICATIONS

"Urbanears Humlan Black," Urbanears Humlan Black Product Information, [retrieved from the internet on Nov. 18, 2014], URL <www.urbanears.com/headphones/humlan/humlan-black/>, pp. 1-10.
"Urbanears Plattan ADV Headphone", Urbanears Plattan ADV Product Information, [retrieved from the internet on Nov. 18, 2014], URL <www.urbanears.com/headphones/adv-plattan-adv-black/>, pp. 1-13.
International Search Report for PCT International Application No. PCT/US2016/015021, dated Apr. 1, 2016, 2 pages.

* cited by examiner

COMFORT HEADBAND FOR HEARING PROTECTORS

CROSS REFERENCE TO RELATED APPLICATIONS

This application is a national stage filing under 35 U.S.C. 371 of PCT/US2016/015021, filed Jan. 27, 2016, which claims the benefit of provisional Application No. 62/111,532, filed Feb. 3, 2015, the disclosure of which is incorporated by reference in its/their entirety herein.

BACKGROUND

People frequently wear hearing protection when they are in loud or noisy environments. Hearing protection can reduce the amount of noise the user's ears are exposed to. However, users often experience discomfort after wearing a hearing protection headset for an extended period of time.

SUMMARY

A hearing protection apparatus is provided. The apparatus comprises a removable compressible pad having a top portion and a bottom portion wherein the compressible pad is configured to be secured to the headband when the apparatus is worn. The compressible pad can provide increased comfort and an improved fit to the user. The headband design can have one or more openings to accommodate the compressible pad. The openings in the headband can help dissipate heat when the compressible pad is removed. The headband openings can also help improve comfort for users that wear baseball caps and other hats by providing additional space to accommodate any protruding items from the top of the caps or hats, preventing the item from being pressed against the top of the user's head.

In one example, an apparatus for hearing protection with a removable compressible pad includes first and second ear cups, a headband having a first end affixed to a first ear cup and a second end affixed to a second ear cup. The headband has a central line from the first end to the second end, and the headband defines one or more openings along the central line that span the thickness of the headband from the top side to the bottom side. The removable compressible pad has a top portion and a bottom portion wherein the compressible pad is configured to be secured to the headband when the apparatus is worn, and the compressible pad spans at least a portion of at least one or more of the openings in the headband. The bottom portion of the pad is configured to contact the head of a user when the apparatus is worn and the top portion contacts the top surface of the headband. The top portion is fastened to the bottom portion through the one or more openings of the headband by various attachment means. The compressible pad can provide increased comfort to the user of the apparatus. The compressible pad can also provide an improved fit for the apparatus on different head sizes. The compressible pad can include one or more openings.

In an embodiment, the apparatus can include a removable compressible pad wherein the compressible pad has a single piece construction. The compressible pad can be a single piece with a top surface, a bottom surface, and an attachment region comprising a channel or groove wherein the attachment region is disposed between the top surface and bottom surface. The channel or grove can be configured to fit around a portion of the headband and position the compressible pad inside the one or more openings so that the bottom surface of the compressible pad contacts the user's head when the apparatus is worn.

In an example, an apparatus for hearing protection can also include a sound input source, such as a microphone, disposed on the apparatus. The sound input source is configured to pick up an input sound wave from the environment and to convert the input sound wave to an incoming signal. The apparatus also includes a processor that is configured to receive the incoming signal and create an output signal. The apparatus can further include a speaker disposed on the apparatus. The speaker is configured to produce the output from the processor.

BRIEF DESCRIPTION OF THE DRAWINGS

The present embodiments may be more completely understood in connection with the following drawings, in which.

While the present embodiments are susceptible to various modifications and alternative forms, specifics thereof have been shown by way of example and drawings, and will be described in detail. It should be understood, however, that the embodiments are not limited to the particular embodiments described. On the contrary, the intention is to cover modifications, equivalents, and alternatives falling within the spirit and scope of the invention.

DETAILED DESCRIPTION

The embodiments described herein are not intended to be exhaustive or to limit the claims to the precise forms disclosed in the following detailed description. Rather, the embodiments are chosen and described so that others skilled in the art can appreciate and understand the principles and practices of the present embodiments.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

Figure 1:
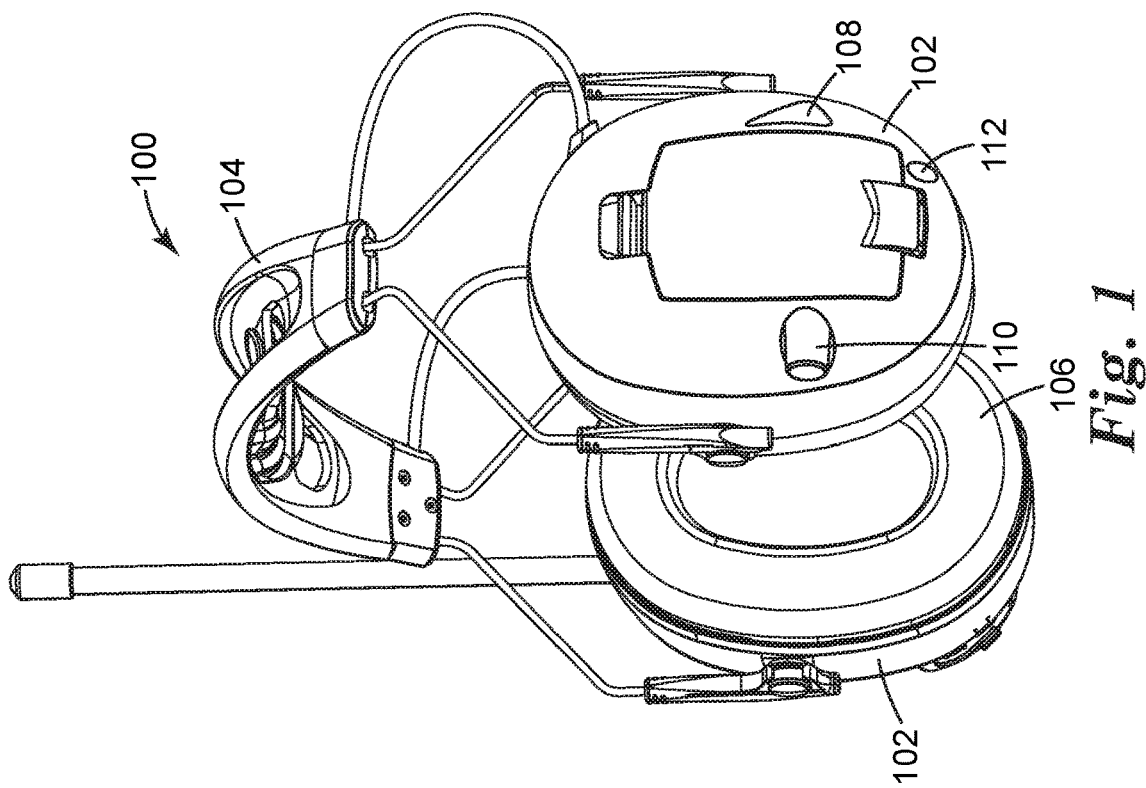
FIG. 1 is a perspective view of a headset, according to an embodiment.

FIG. 1 is a perspective view of a hearing protection headset 100. In an embodiment, the headset 100 can include an ear cup 102 and a headband 104. The headset 100 can include two ear cups 102. The headband 104 can couple a first ear cup 102 with a second ear cup 102. The headband 104 can be arced, such as to extend over the top of a user's head while the headset 100 is in use. The headband has a central line that runs along its length from one end to another. The headband 104 can be flexible, such as to allow the user to spread the first ear cup 102 from the second ear cup 102 when the user is putting on the headset 100. The headband design can comprise a single band, twin bands, or others. The headband can also comprise one or more openings.

The ear cups 102 can be configured to fit at least partially around a user's ear, and be disposed on the side of a user's head while in use. The ear cup 102 can define a cavity. The cavity can be configured for a user's ear, a human ear, to fit within, while the user is wearing the headset 100. The ear cup 102 can include a seal ring 106. The seal ring 106 can be ring shaped, such as to extend around the user's ear. The seal ring 106 can be flexible and able to conform to the user's head. The seal ring 106 can provide a seal between the ear cup 102 and the user's head, such as to reduce the amount of noise or sound waves that reach the user's ear, thereby at least partially protecting the user's ear from external noises. The seal ring 106 can include leather, cloth, rubber, plastic, or a polymer, such as polyurethane.

The headband 104 can include a compressible pad made of a compressible material, such as to at least partially conform to the user's head and increase the user's comfort. The use of the term "compressible" means that the thickness of the pad can be decreased by applying pressure. In an embodiment, the compressible pad may also be relatively thick to improve the fit of the headset on smaller head sizes. The compressible pad can comprise a top layer and a bottom layer that can be fastened to each other through openings in the headband. The compressible pad can be removable, meaning it can be taken off and separated from the headband and/or headset. The compressible pad can also include one or more openings.

Figure 2:
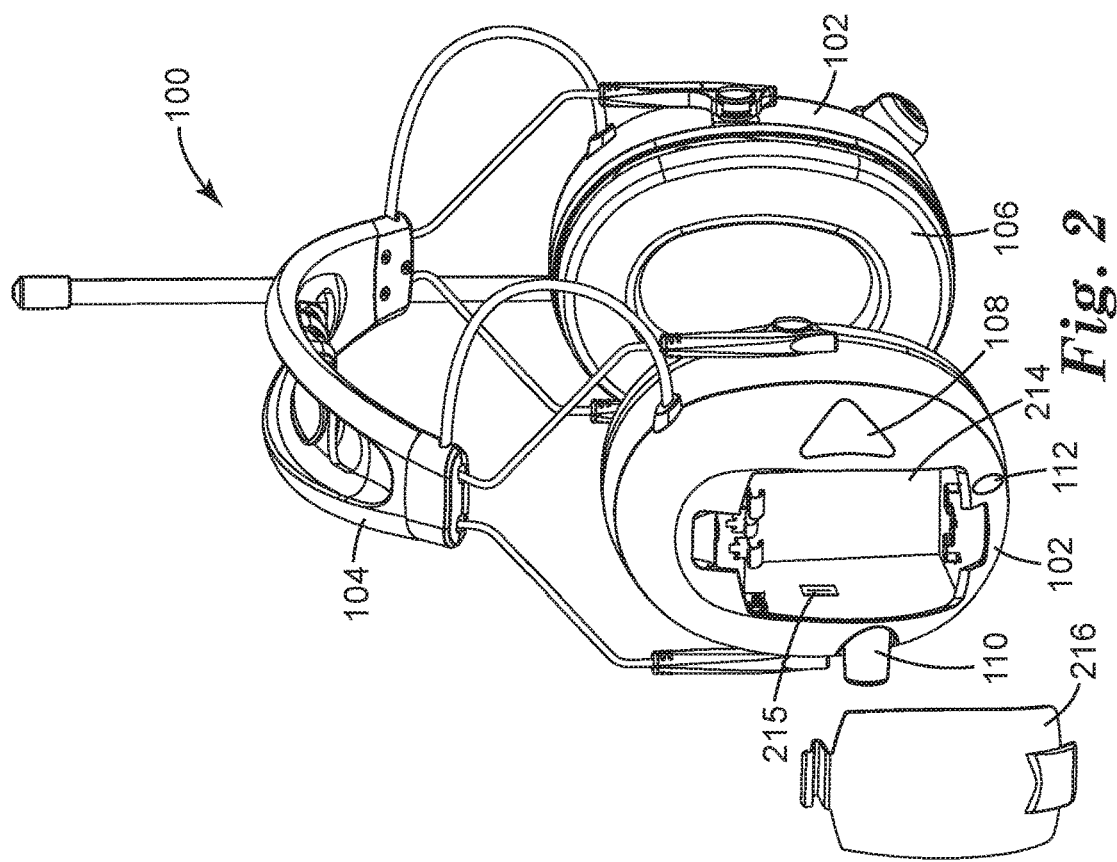
FIG. 2 is a perspective view of a headset, according to an embodiment.

Some embodiments of ear protection headsets are passive, with no electronic components. Some embodiments of ear protection headsets include electronic components and active controls to enable the user to better hear desirable sound in the noisy environment. Both passive and active types of embodiments can use the compressible pad described herein. FIG. 1 and FIG. 2 show an active headset 100 with electronic components and active controls. Alternative embodiments could include fewer electronic components or could lack electronic components. The headset 100 can include a sound input source 108. In one embodiment, one or both of the ear cups 102 can include a sound input source 108. In an embodiment, the sound input source 108 can comprise a microphone. In an embodiment, there is one microphone 108 on each of two ear cups 102. In an embodiment, there can be more than one microphone 108 on one or both of the ear cups 102. In one embodiment, one or more microphones 108 are located at other locations on the headset 100. The microphone 108 can be disposed on the outside surface of the ear cup 102 opposite the cavity. The microphone 108 can pick up sound and noise from the surrounding environment. The microphone 108 can be inset, such that the microphone 108 does not extend past the outer surface of the ear cup 102. In an embodiment with two ear cups 102, each ear cup 102 can include a microphone 108. In another embodiment with two ear cups 102, only one ear cup 102 includes a microphone 108. In another embodiment with two ear cups 102, one microphone 108 is positioned on a headband portion. The noises and sounds picked up by the microphone 108 can be relayed to the user through a speaker in the cavity of the ear cup 102.

One of the ear cups 102 can include a knob 110. The user can rotate the knob 110 to control the electronics of the headset 100, such as to turn the electronics "ON" or "OFF", or to increase or decrease the volume from the speakers in the ear cups 102.

The ear cups 102 can include an input connection 112. The input connection 112 can allow a user to connect an external audio device into the headset 100, such as an AM/FM radio, a two-way radio, an MP3 player, a cellphone, or the like. The user can hear the external audio device through the one or more speakers disposed in the ear cups 102. In an embodiment, the input connection 112 can accommodate a 3.5 mm audio input. In an embodiment, the external audio device can be connected to the headset 100 through a wireless connection, such as Bluetooth connection. In an embodiment, an input to the headset can include a Bluetooth connection. In an embodiment, the external audio device can be built in or integral with the headset 100.

The ear cups 102 can include a battery compartment 214. The battery compartment 214 can house one or more batteries or battery packs. The batteries can be used to power the electronic components of the headset 100. In an embodiment, two AA batteries can be disposed within the battery compartment 214. In an embodiment, the AA batteries can include an alkaline AA battery, a carbon AA battery, a lithium AA battery, a nickel-metal hydride AA battery, or a nickel-cadmium AA battery. In an embodiment, a rechargeable battery pack can be disposed within the battery compartment. In an embodiment, the rechargeable battery pack can use a lithium ion cell battery. A charging port 215 can be disposed on one or more of the ear cups. In an embodiment, the charging port can be configured to receive a cable for recharging the rechargeable battery pack. A battery door 216 can at least partially enclose the battery compartment 214. The battery door 216 can be configured to be removed from the headset 100 when access to the batteries are desired, such as to replace the batteries.

Figure 3:
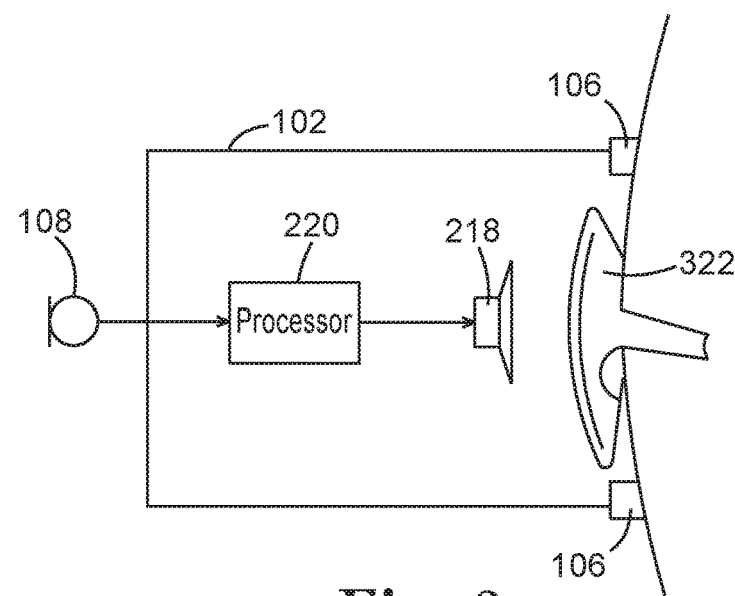
FIG. 3 is a schematic diagram of a certain headset components, according to an embodiment.

FIG. 3 is a schematic of some components of an active hearing protector 101. Each ear cup 102 can include a speaker 218, shown in FIG. 3. The speaker 218 can produce an output, such as a sound wave. Incoming sound and noise from sound input 108 can be input into a processor 220 and be processed, such as to eliminate at least some of the noise, to produce an output through the speaker 218. As used herein, the term sound refers to desirable audio information while the term noise refers to undesirable audio information. The speaker 218 can provide sound to the user, such as desirable audio. Desirable audio can include conversations, commands, warnings or other communications, such as communications between two people. The input from each microphone can be processed to eliminate at least some of the noise, such as undesirable noises. Undesirable noises can include mechanical noises, noises from ventilation systems, distant conversations, impulse noises, grinding, squeaking, engine noises, gun shots, explosions and the other similar noises.

The speaker 218 can relay sounds from the surrounding environment picked up by the sound input 108. The speaker 218 can relay sounds from an external audio device connected from the input connection 112, or from an audio device integrated into the headset. The output from the speaker 218 can be limited to a maximum output level, such as to protect the user's ears. In different embodiments, the maximum output level from the speaker 218 due to sound from the microphone can be at least 80 dB(A), not more than 90 dB(A), at least 70 dB(A), not more than 100 dB(A), and combinations of these constraints. In an embodiment, the output from the speaker 218 is limited to 82 dB(A) when the ambient sound level is less than 106 dB(A), regardless of how high the user has the volume turned up. In an embodiment, the output from the speaker 218 is limited to 85 dB(A) when the ambient sound level is less than 106 dB(A), regardless of how high the user has the volume turned up. In an embodiment, the output from the speaker 218 is limited to 82 dB(A), regardless of how high the user has the volume turned up. In an embodiment, the output from the speaker 218 is limited to 85 dB(A), regardless of how high the user has the volume turned up. In an embodiment, the output from the speaker 218 can be limited to 82 dB(A) when an external audio device is connected to the input connection 112. The sounds picked up by the microphone 108 can be processed before they are produced as output from the speaker 218. The processing can increase the quality or clarity of what the user hears, such as by reducing background noise, suppressing impulse noises or keeping an input level constant. In one embodiment where each of two ear cups 103 has a microphone 108, the incoming sound and noise is processed by a single processor. In another embodiment where each of the two ear cups 102 has a microphone 108, the incoming sound and noise is processed by separate processors.

The individual features described herein can be present in various embodiments. Also combinations of the individual features described herein can be present in various embodiments. The compressible pad can comprise a separate top layer and bottom layer. The compressible pad can comprise a fabric, skinned foam, open-cell foam, closed-cell foam, a woven or nonwoven fabric, a woven or nonwoven mesh, natural or synthetic leather, or a low density silicone. The top and bottom portions of the compressible pad can be made of the same materials or they can be made of different materials. The compressible pad can also be a compound construction with different portions or layers of the pad composed of different materials or different combinations of materials. These different materials can include mesh fabric, foam, polypropylene stiffeners, and ABS polymers. In an embodiment, the compressible pad can be constructed using the following materials from top to bottom: acrylonitrile butadiene styrene (ABS) polymer attachment structure molded into mesh fabric, foam, polypropylene stiffeners, foam, and mesh fabric. In one embodiment, the ABS polymer attachment structures are pillars or other structures that are received by openings in the headband. The compressible pad can comprise one or more openings that can correspond to the openings in the headband. The compressible pad can cover all the openings in the headband or it can only cover some of the openings in the headband.

Figure 4:
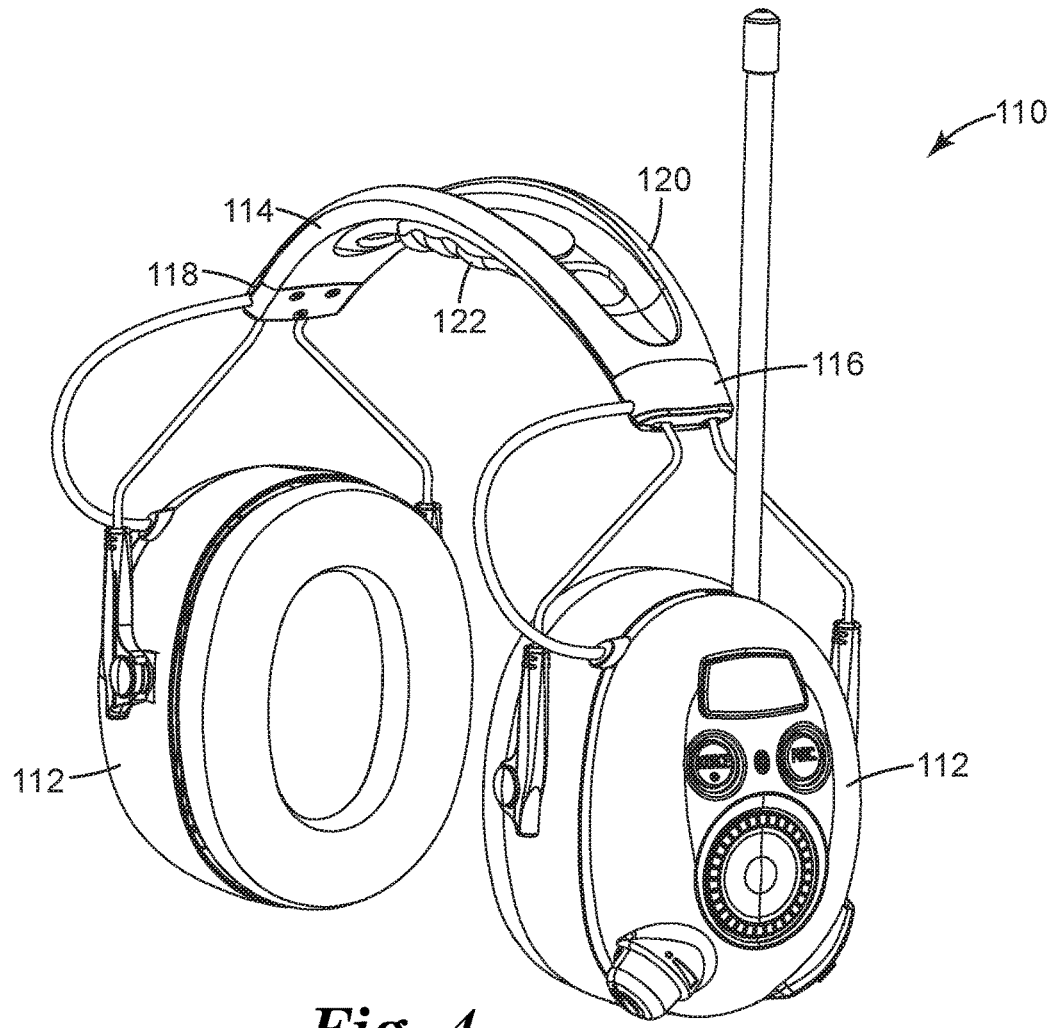
FIG. 4 is a perspective view of a headset, according to another embodiment.

The compressible pad can be used with a hearing protection apparatus that comprises a headband with one or more openings. In FIG. 4, a hearing protection apparatus 110 is shown with first and second ear cups 112, and a headband 114 with a first end 116 affixed to one ear cup and a second end 118 affixed to the other ear cup. The headband has a central line that runs along its length from first end 116 to second end 118. The headband has an opening 120 along the central line, and the opening is partially covered by a compressible pad 122 which is secured to the headband of the apparatus. The headband 114 can be a wire frame headband manufactured with a rubber overmold material. The compressible pad comprises two portions; a bottom portion that contacts the head of the user when the apparatus is worn, and a top portion that contacts the headband. The top and bottom portions of the compressible pad also comprise attachment means for fastening the top portion to the bottom portion through one or more of the openings in the headband.

Figure 5:
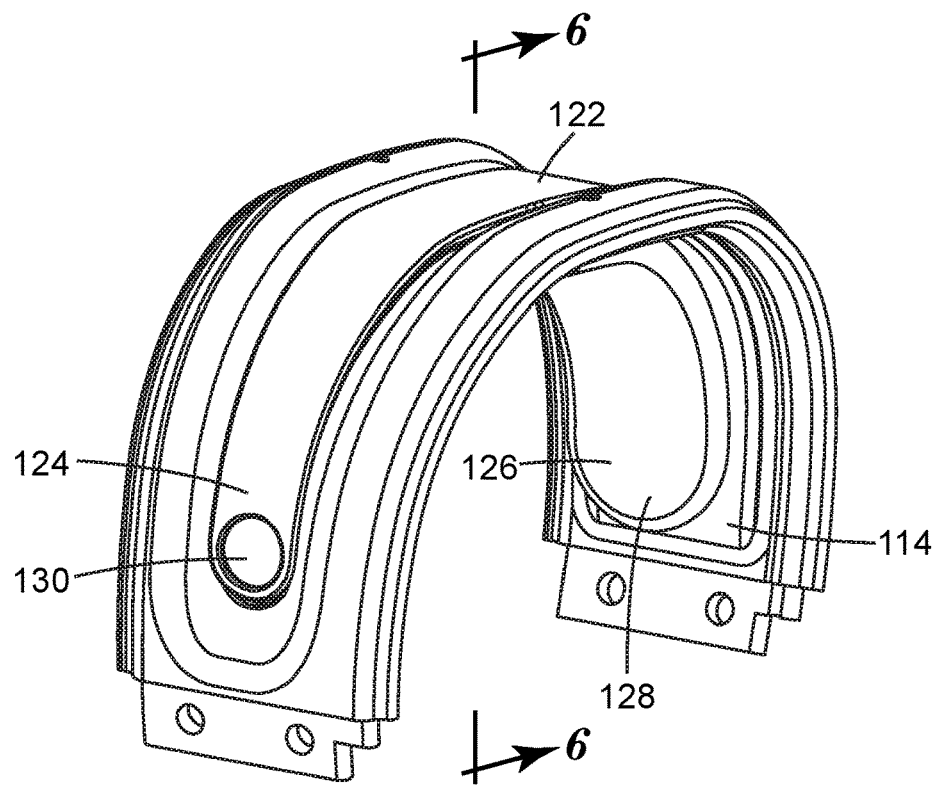
FIG. 5 is a perspective view showing an embodiment of a comfort pad.
Figure 6:
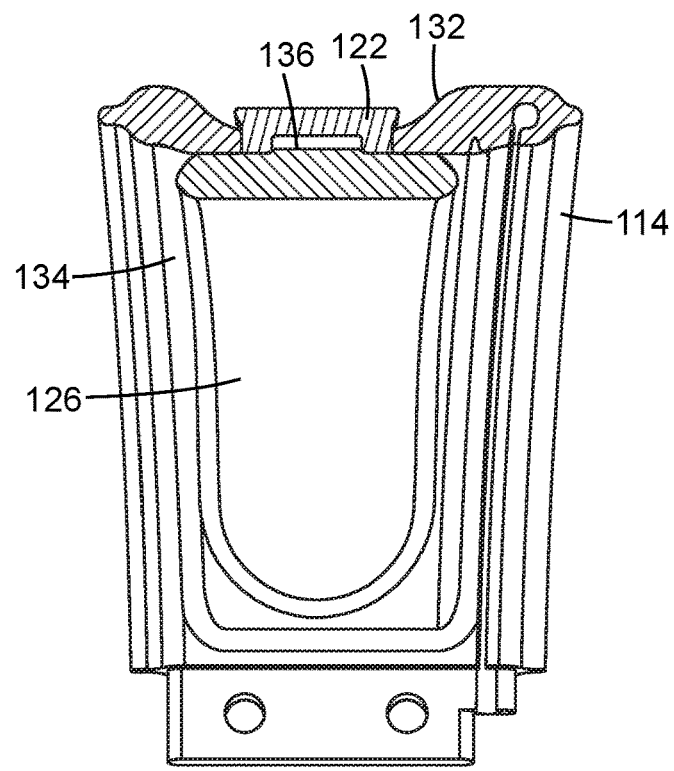
FIG. 6 is a perspective view showing an embodiment of a cross-section of the comfort pad of FIG. 5, along line 6-6 of FIG. 5.

The top portion of the compressible pad can comprise a top material layer 122 and a bottom material layer 126 shown in FIG. 5. The top material layer includes a first end region 124 and a second end region 125 (shown in FIG. 7b). The bottom material layer 126 includes a first end region 127 (shown in FIG. 7b) and a second end region 128. The first end region of the top layer is attached to the first end region of the bottom layer through an opening in the headband 114 using attachment means 130. FIG. 6 shows a cross section view of the embodiment of the compressible pad shown in FIG. 5. The headband 114 has a top surface 132 and a bottom surface 134. When positioned on the headband, the top layer 122 contacts the top surface 132 of the headband and bottom layer 126 contacts the bottom surface 134 of the headband. In FIG. 5 and FIG. 6, the top and bottom layers completely cover opening 136 in the headband. In embodiments, the top layer, the bottom layer, or both layers may only partially cover the openings in the headband. In FIG. 6, the width of top layer 122 is less than the width of bottom layer 126. In other embodiments, the two layers can have substantially equal widths. The thickness of top layer 122 can be less than the thickness of bottom layer 126. In other embodiments, the two layers can have substantially equal thickness.

Bottom layer 126 extends below the bottom surface 134 to provide cushioning to the user. Depending on the amount of cushioning desired, the distance that the bottom layer may extend below the bottom surface of the headband can vary. In embodiments, the bottom layer of the compressible pad may extend no less than 5 mm, no less than 10 mm, or no less than 20 mm below the bottom surface of the headband. The bottom layer may extend further below the bottom surface of the headband to provide an improved fit for the headband for smaller head sizes. In embodiments, the bottom layer of the compressible pad may extend no more than 40 mm, no more than 30, or no more than 25 mm below the bottom surface of the headband.

Figure 7A:
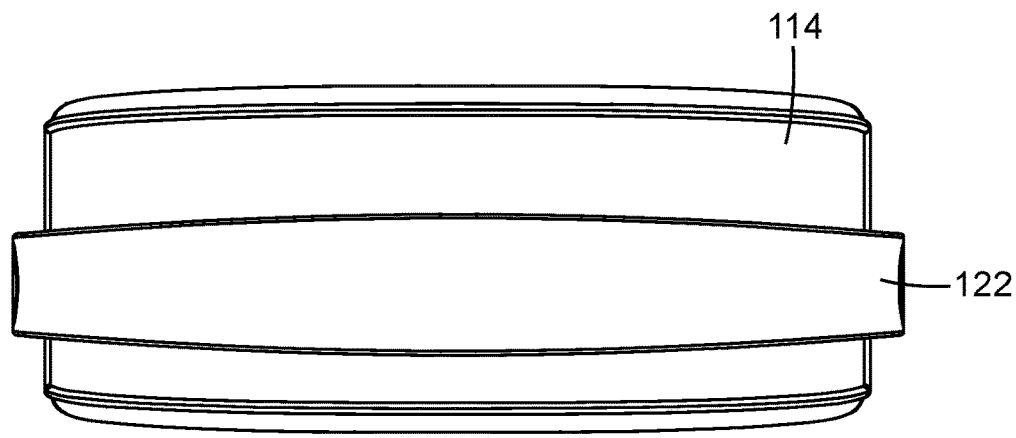
FIG. 7a is a top view of an embodiment of the comfort pad.
Figure 7B:
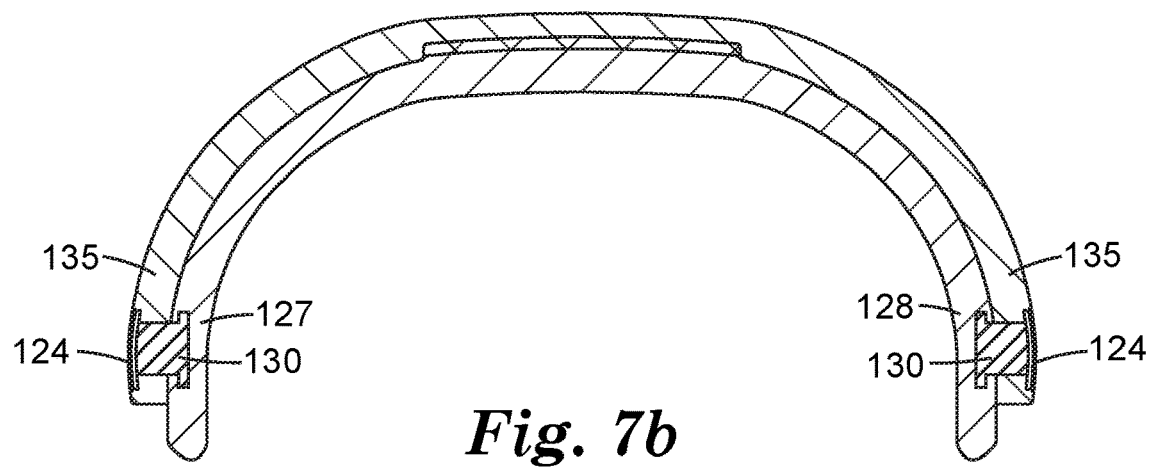
FIG. 7b is a cross-section view of an embodiment of the comfort pad on a headband.

FIG. 7a and FIG. 7b show a different view of the compressible pad on the headband 114. The top layer 122 contacts the top surface of the headband and bottom layer 126 contacts the bottom surface of the headband. The top layer includes a first end region 124 and a second end region 125. The bottom material layer 126 includes a first end region 127 and a second end region 128. The first end region of the top layer is attached to the first end region of the bottom layer through openings 135 in the headband 114, using attachment means 130. In FIG. 7b, the length of the top layer is less than the length of the bottom layer. In other embodiments, the two layers can have substantially equal lengths.

The compressible pad can include attachment means than can fasten the top portion of the pad to the bottom portion. The attachment means for the pad can comprise a snap fit, a press fit, an injection-molded insert, a hook and loop fastener, one or more magnets, a friction fit, buttons, or a shaped insert and matching opening. The attachment means can also be used to secure the compressible pad against the headband. The attachment means can include an attachment region having channel or groove configured to mate with a portion of the headband and position the compressible pad inside the one or more openings of the headband. For example, the channel or groove can mate with an edge of an opening of the headband, as will be further discussed herein with respect to FIGS. 12-16.

Figure 8:
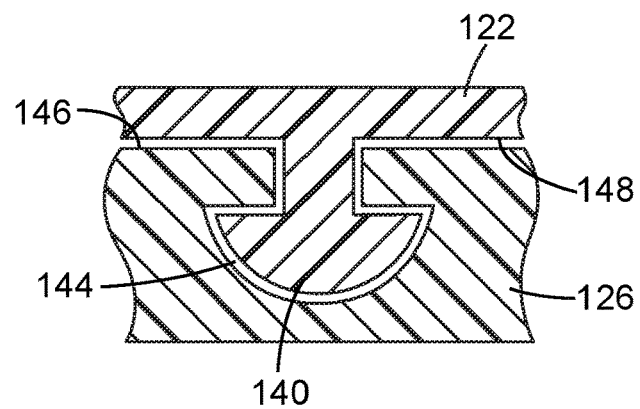
FIG. 8 is a cross-section view of an attachment means for a comfort pad, according to an embodiment.

The attachment devices used for the attachment means can include different or unique shapes. FIG. 8 shows an embodiment of an attachment means that uses a shaped insert with a matching opening as the attachment device. The attachment device is disposed on the bottom surface 148 of top layer 122 and on the top surface 146 of bottom layer 126. In this embodiment, top layer 122 includes a male-type insert 140 that fits into a female-type opening 144 in bottom layer 126. The embodiment in FIG. 7b and FIG. 8 shows an insert with one end having a mushroom-cap shape, but other shapes can be used as well, such as pillar shapes or mushroom-cap shapes with a flat top. The distance that the insert 140 from the top layer 122 extends into the bottom layer 126 can vary depending on the types of materials used and the thickness of the materials in the top and bottom layers, as well as the type of material used in the attachment means. In an embodiment, an insert from the top layer can extend through the entire thickness of the bottom layer.

Figure 9:
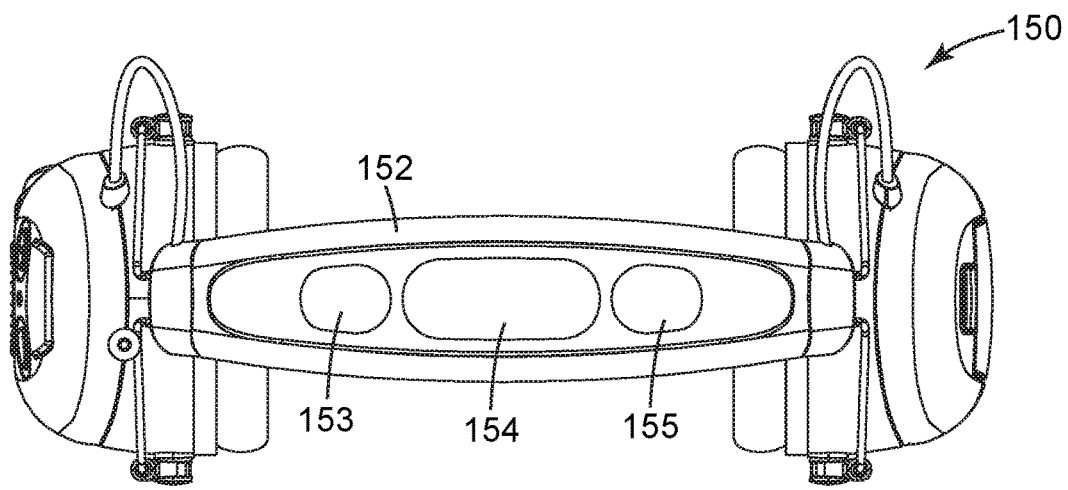
FIG. 9 is a perspective view of a headset, showing an embodiment with one or more openings in the headband.

The compressible pad can be used in a hearing protection apparatus that has more than one opening in the headband. The openings in the headband can be the same size or they can be different sizes. The compressible pad can also contain one or more openings that align with one or more openings in the headband. Additional openings in the compressible pad can improve the comfort qualities of the compressible pad such as helping heat escape from the head of the user or accommodating additional protrusions that may extend from caps or hats the user may wear. In an embodiment, the number of openings in the compressible pad is less than the number of openings in the headband. In an embodiment, the number of openings in the compressible pad is greater than the number of openings in the headband. A view of a hearing protection apparatus with more than one opening in the headband is shown in FIG. 9. The headset 150 includes a headband 152 with openings, 153, 154, and 155.

Figure 10A:
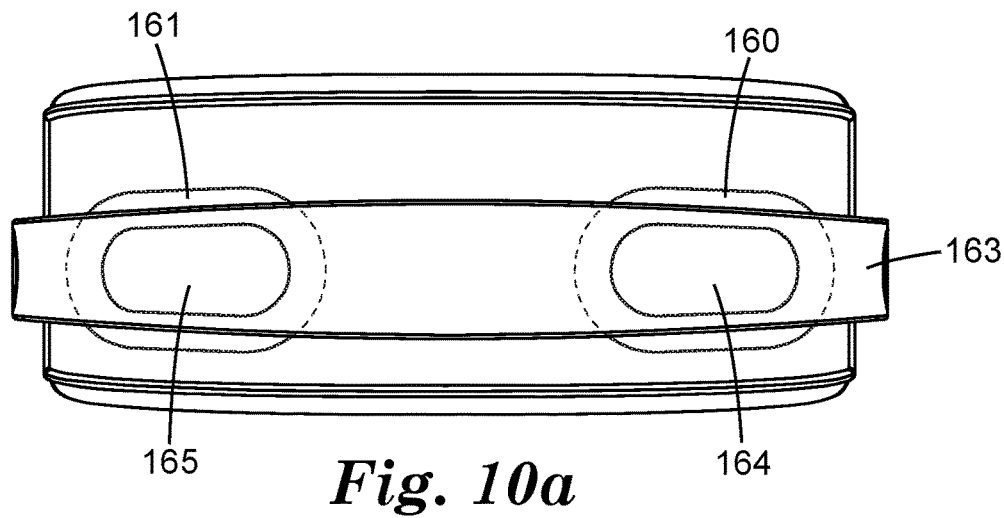
FIG. 10a is a perspective view of an embodiment of the comfort pad showing more than one opening in the comfort pad.
Figure 10B:
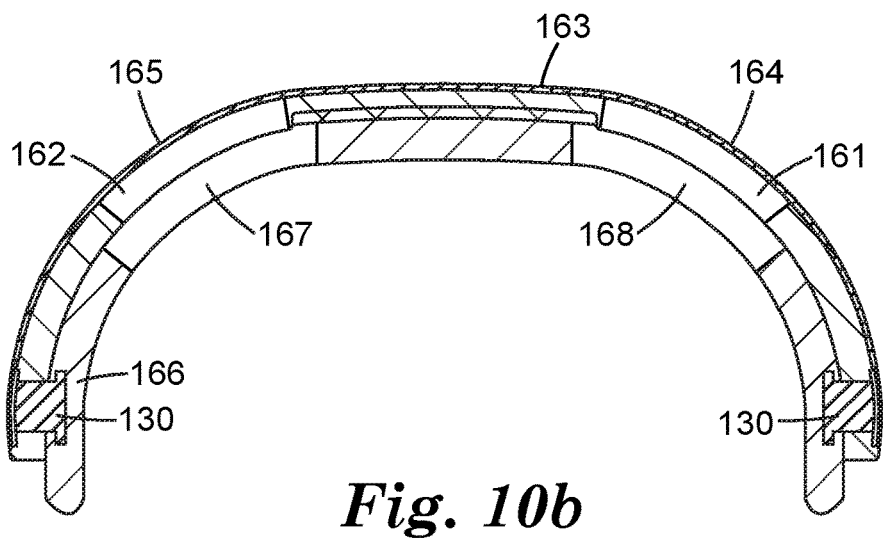
FIG. 10b is a cross-section view of an embodiment of the comfort pad on a headband showing more than one opening in the comfort pad and headband.

FIG. 10a and FIG. 10b show a perspective view of a compressible pad secured to a headband. The headband 160 contains openings 161 and 162. The top layer 163 of the compressible pad has openings 164 and 165 shown that are smaller than the openings in the headband. In other embodiments, the openings in the top layer can be larger than the openings in the headband, or the openings in the top layer can be approximately the same size as the openings in the headband. The bottom layer 166 has openings 167 and 168 that are aligned with the headband openings 161 and 162. In the cross-section view shown in FIG. 10b, the bottom layer openings shown are approximately the same size as the headband openings. In other embodiments, the openings in the bottom layer can be larger than the openings in the headband, or the openings in the bottom layer can be smaller than the openings in the headband.

In other embodiments, the compressible pad used in the apparatus can be constructed as a single piece. In this type of embodiment, the compressible pad can have a top surface, a bottom surface, and an attachment region disposed between the top surface and the bottom surface. The attachment region can include a channel or groove that is configured to receive a portion of the headband and position at least a portion of the compressible pad inside the one or more openings so that the bottom surface of the compressible pad contacts the head of a user when the apparatus is worn. The compressible pad can also include two or more attachment regions, each attachment region with a separate channel or groove configured to receive or mate with a portion of the headband and position portions of the compressible pad inside two or more openings. In embodiments, the compressible pad is placed into the one or more openings of the headband by deforming the pad, such as by squeezing or bending, and placing it inside the openings so that the channel or groove on the pad can fit against a portion of the headband. Upon being placed into the opening in the headband, the compressible pad can then expand and form a compressible fit with the headband, holding the compressible pad in place on the apparatus. The compressible pad can then be removed from the headband by deforming the pad, for example, by squeezing again, to separate the channel or groove on the pad from the headband, and then pulling the compressible pad out from the openings.

In an embodiment, the attachment region of the compressible pad comprises a material with different properties from the material used for the bottom surface of the compressible pad, and the attachment region can use other designs besides a channel or groove to provide a fit. In an embodiment, the material used in the attachment region can have certain material properties that can be used to fit portions of the compressible pad inside the one or more openings. In an embodiment, portions of the compressible pad that fit into the one or more openings can be constructed of a stiffer material than the material used in the portions of the compressible pad that contact the user's head. In such embodiments, the portions of the compressible pad made of stiffer materials can be sized to fit into the one or more openings and can be pushed into the one or more openings, providing a friction fit that positions the compressible pad on the headband. In some embodiments, the material of the headband is a soft overmold material which defines one or more openings which receive one or more attachment structure made of a stiffer material portion of the compressible pad. In this type of embodiment, an element of deformation that enhances the friction fit comes from the material of the headband rather than from the material of the pad.

Figure 12:
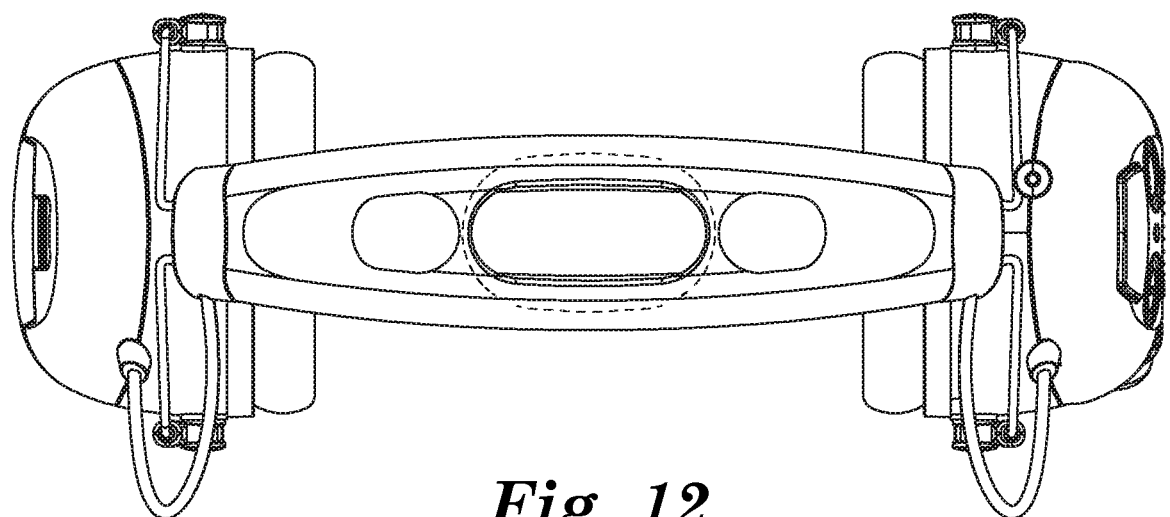
FIG. 12 is a top view of the headset embodiment of FIGS. 1, 2 and 9, where the headband is shown in dashed lines, so that a compressible pad can be viewed within the context of the headband and its three openings.
Figure 13:
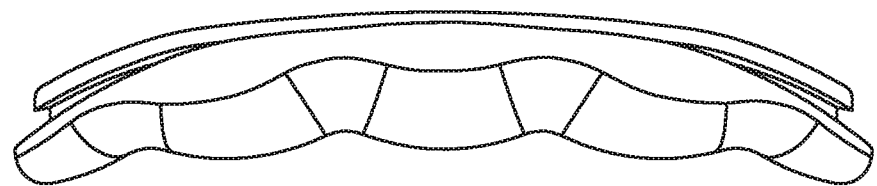
FIG. 13 is a side, bottom perspective view of the headset embodiment of FIG. 12, where the headband is shown in dashed lines, so that the compressible pad can be viewed within the context of the headband and its three openings.

FIGS. 12-15 show embodiments of a compressible pad constructed as a single piece used with an apparatus that includes a headband with more than one opening along the central line of the headband. FIGS. 1, 2 & 9 show the headband with more than one opening without the compressible pad. As shown in FIGS. 1, 2, 9 and 12, the headset includes a headband with a central opening that is larger than the two other openings. FIG. 12 is a top view of the headset where the headband is shown in dashed lines, so that the compressible pad can be viewed within the context of the headband and the three openings. The compressible pad fits into the central opening in the headband. The length and width of the top surface of the compressible pad are larger than the length and width of the central opening, allowing the top surface to completely cover the opening. In other embodiments, either the length or width of the top surface could be smaller than the length or width of the opening, allowing the top surface to only cover a portion of the opening. FIG. 13 is a side, bottom perspective view of the headset embodiment of FIG. 12, where the headband is shown in dashed lines, so that the compressible pad can be viewed within the context of the headband and its three openings. In FIG. 13, it can be seen that a portion of the compressible pad also extends underneath the opening in the headband and is configured so that the bottom surface of the compressible pad contacts the head of a user when worn.

Figure 14:
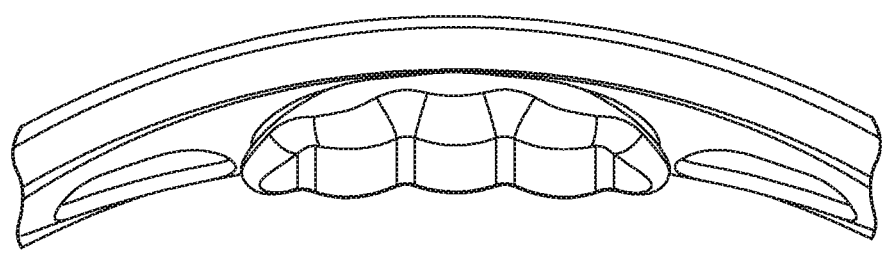
FIG. 14 is a side view of the compressible pad of the headset embodiment of FIG. 12, shown alone and separate from the remainder of the headband.
Figure 15:
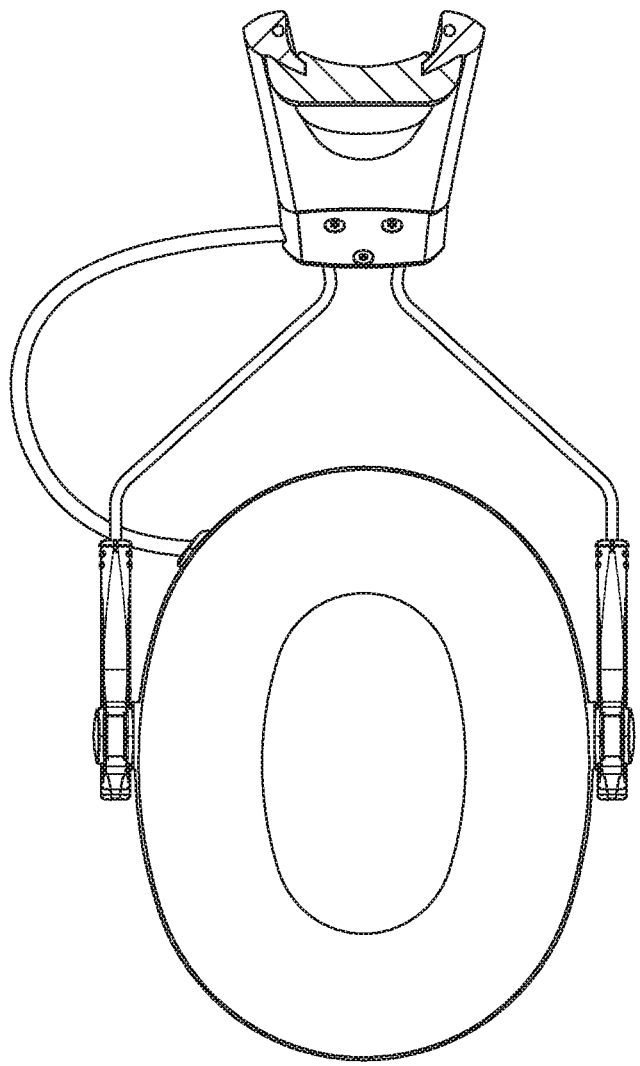
FIG. 15 is a cross-section view of the headset embodiment of FIG. 12, including a one-piece compressible pad.

The one-piece compressible pad is positioned and held in place inside the central opening using an attachment region that is disposed between the top surface of the pad and the bottom surface of the pad. FIG. 14 is a side view of the compressible pad alone. In FIG. 14, the attachment region includes a channel or groove that runs from a first end region of the compressible pad to a second end region of the compressible pad. The channel or groove is configured to fit around a portion of the side of the headband and position at least a portion of the compressible pad against the headband. In an embodiment, the channel or groove can be disposed in the attachment region on a peripheral surface of the compressible pad. In an embodiment, the channel or groove can run along the entire circumference of a peripheral surface of the attachment region. When positioned in the opening, the compressible pad forms a compressible fit with the sides of the headband. A cross-section view of an embodiment of an apparatus including a one-piece compressible pad is shown in FIG. 15. The channel or groove in the attachment region fits over portions of the sides of the headband, positioning the compressible pad inside the opening so that the top surface of the compressible pad is above the attachment region, and the bottom surface of the pad is configured to contact the head of a user when the apparatus is worn. The top surface and bottom surface of the compressible pad are wider than the opening so the compressible pad covers the entire width of the opening.

Figure 11:
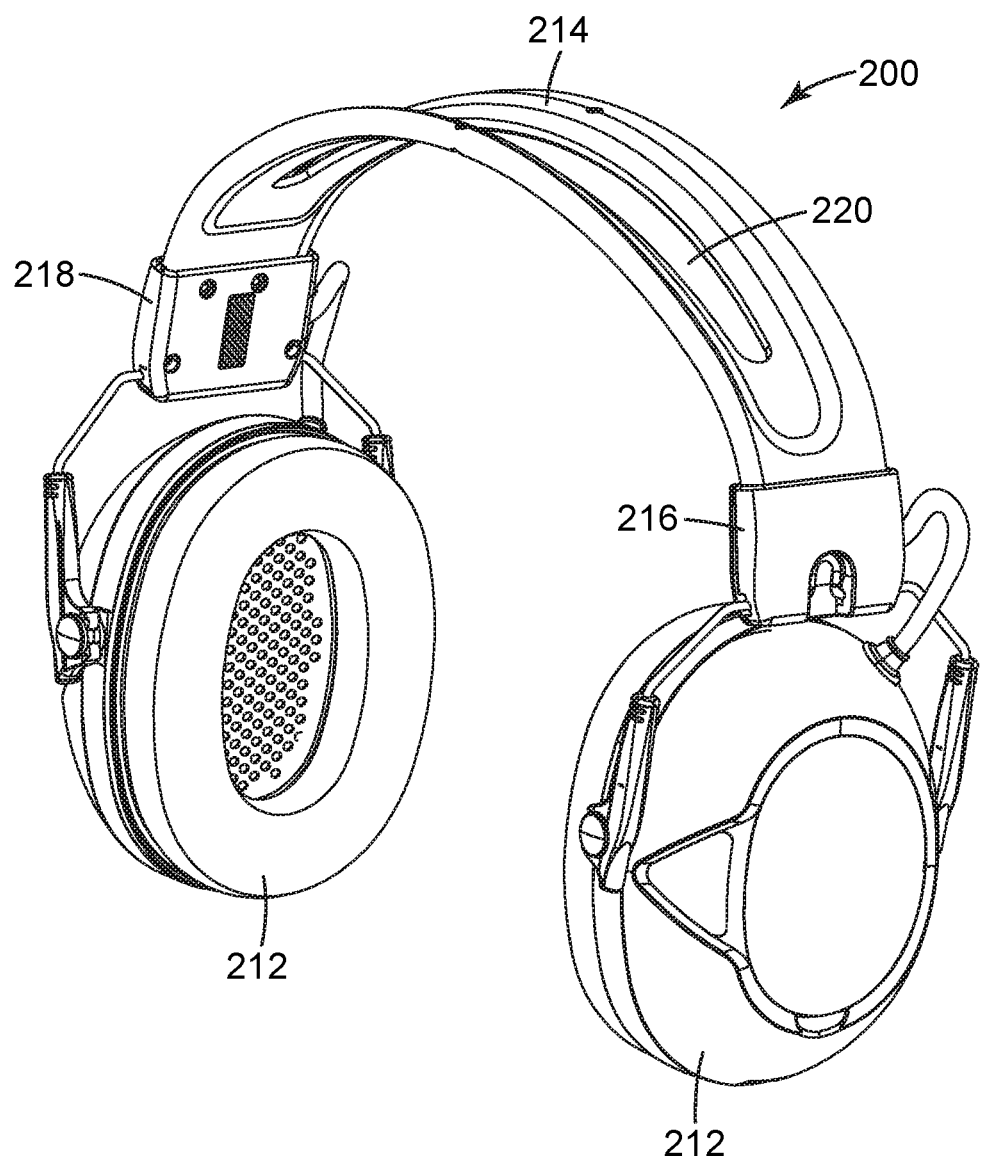
FIG. 11 is a perspective view of a headset without a comfort pad in the headband.
Figure 16:
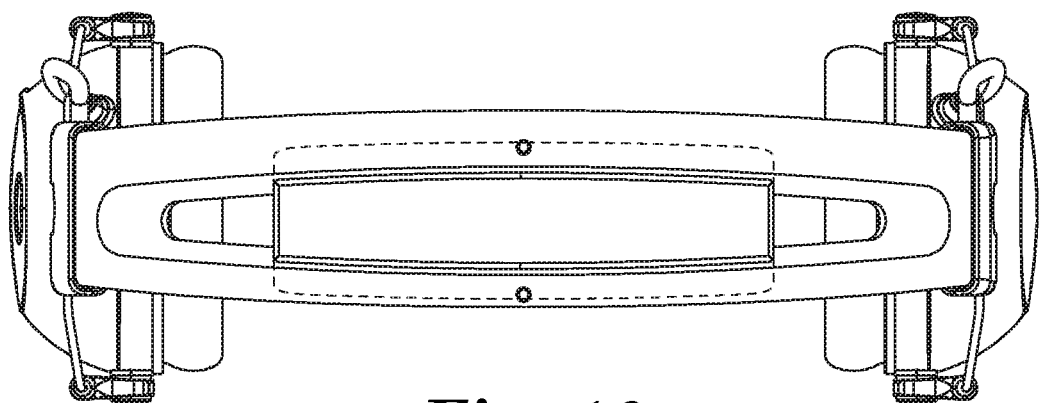
FIG. 16 is a top view of the headset embodiment of FIGS. 4 and 11, showing a compressible pad positioned within the single opening defined by the remainder of the headset.

FIGS. 4, 11 and 16-19 show embodiments of a compressible pad constructed as a single piece used with an apparatus that includes a headband with a single long opening. In FIG. 16, the headset includes a headband with a single opening that runs along the central line of the headband from a first end region of the headband to a second end region of the headband. FIG. 16 is a top view of the headset embodiment of FIGS. 4 and 11, showing a compressible pad positioned within the single opening defined by the remainder of the headset.

Figure 17:
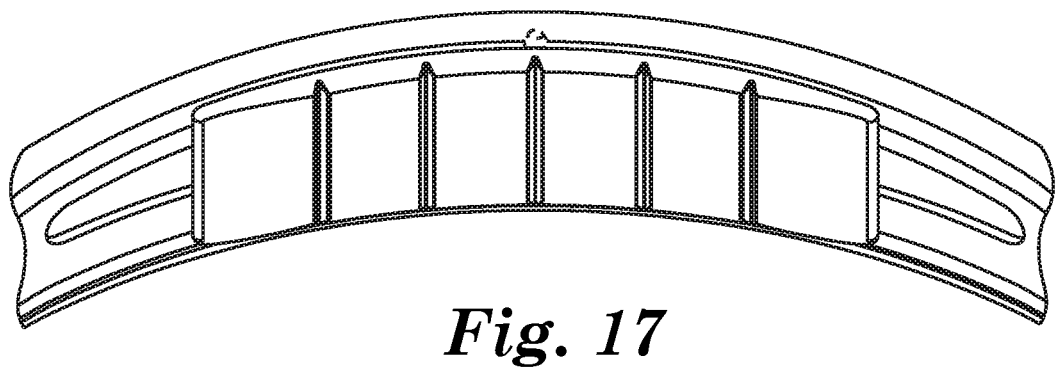
FIG. 17 is a side, bottom perspective view of the headset embodiment of FIG. 16.

The compressible pad fits into the single opening in the headband. The width of the top surface of the compressible pad is larger than the width of the opening, allowing the top surface to completely cover the width of the opening. However, the length of the compressible pad is less than the overall length of the opening, so portions of the opening adjacent to the first end region and second end region of the headband remain uncovered. FIG. 17 is a side, bottom perspective view of the headset embodiment of FIG. 16. In FIG. 17, a portion of the compressible pad also extends underneath the opening in the headband and is configured so that the bottom surface of the compressible pad contacts the head of a user when worn.

Figure 18:
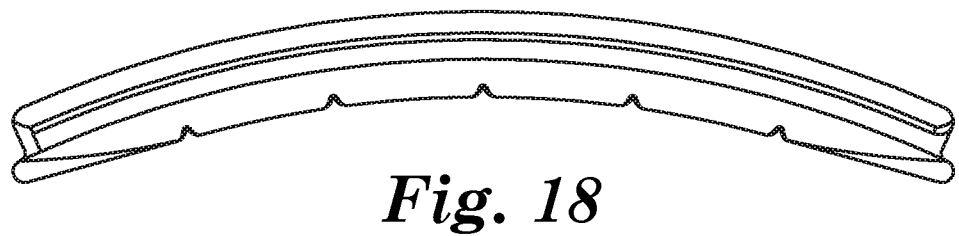
FIG. 18 is a side view of the compressible pad of the headset embodiment of FIG. 16, shown alone and separate from the remainder of the headband.
Figure 19:
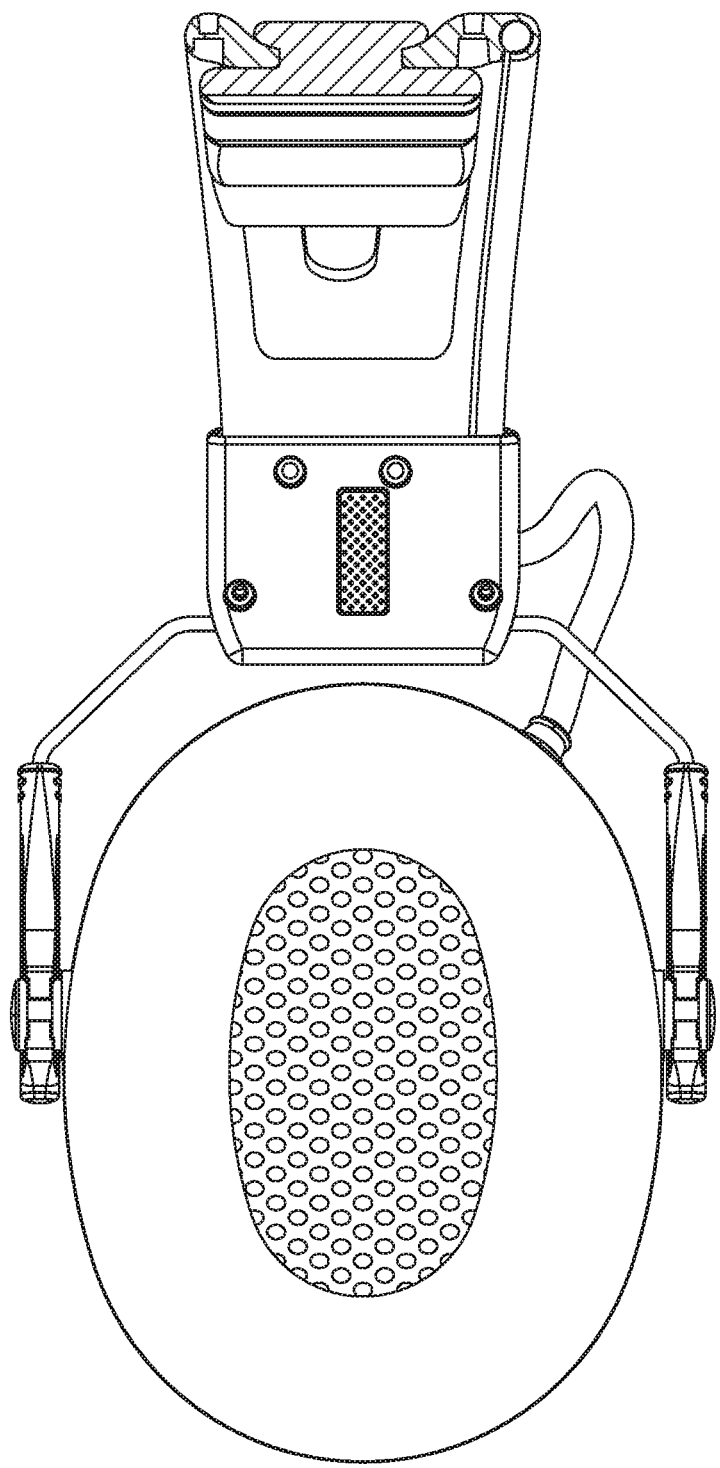
FIG. 19 is a cross-section view of the headset embodiment of FIG. 16, including a one-piece compressible pad.

The one-piece compressible pad is positioned and held in place inside the opening using an attachment region that is disposed between the top surface of the pad and the bottom surface of the pad. In FIG. 18, the attachment region includes a channel or groove that runs from a first end region of the compressible pad to a second end region of the compressible pad. The channel or groove is configured to fit around a portion of the side of the headband and position at least a portion of the compressible pad against the headband. In an embodiment, the channel or groove can be disposed in the attachment region on a peripheral surface of the compressible pad. In an embodiment, the channel or groove can run along the entire circumference of a peripheral surface of the attachment region. When positioned in the opening, the compressible pad forms a compressible fit with the sides of the headband. A cross-section view of an embodiment of an apparatus including a one-piece compressible pad is shown in FIG. 19. The channel or groove in the attachment region fits over portions of the sides of the headband, positioning the compressible pad inside the opening so that the top surface of the compressible pad is above the attachment region, and the bottom surface of the pad is configured to contact the head of a user when the apparatus is worn. The top surface and bottom surface of the compressible pad are wider than the opening so the compressible pad covers the entire width of the opening.

The compressible pad of FIGS. 16-19 defines a number of lateral grooves in one embodiment, which extend from one long side to the other long side, and are defined in the bottom surface of the compressible pad.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which the various embodiments pertain. All publications and patent applications are herein incorporated by reference to the same extent as if each individual publication or patent application was specifically and individually indicated by reference.

The present embodiments have been described with reference to various specific and preferred embodiments and techniques. However, it should be understood that many variations and modifications may be made while remaining within the spirit and scope of the claims.

What is claimed is:

1. An apparatus for hearing protection, comprising:
    first and second ear cups, each ear cup defining a cavity configured to fit a user's ear;
    a headband having a first end affixed to a first ear cup and a second end affixed to a second ear cup, the headband having a central line along its length from the first end to the second end and the headband also having a front side, a back side, a top side, a bottom side, and a thickness extending between the top side and bottom side, the headband defining one or more openings along the central line that span the thickness of the headband from the top side to the bottom side; and
    a removable compressible pad having a top surface and a bottom surface wherein the compressible pad is configured to be secured to the headband when the apparatus is worn, and the compressible pad spans at least a portion of at least one or more of the one or more openings, wherein the bottom surface is configured to contact the head of a user when the apparatus is worn, and wherein the compressible pad is secured to the headband through one or more openings of the headband, wherein the compressible pad comprises one or more openings that are configured to align with one or more openings in the headband when the apparatus is worn.

2. The apparatus of claim 1 wherein the compressible pad comprises a top portion and a bottom portion, and wherein the top portion is fastened to the bottom portion through the one or more openings of the headband.

3. The apparatus of claim 2 wherein the top portion is fastened to the bottom portion through a snap fit, a press fit, an injection-molded insert, a hook and loop fastener, one or more magnets, a friction fit, buttons, or a shaped insert and matching opening.

4. The apparatus of claim 2 wherein the bottom portion of the compressible pad comprises a bottom material layer with first and second end regions, and the top portion of the compressible pad comprises a top material layer with first and second end regions, the first and second material layers each having a thickness, a length, and a width.

5. The apparatus of claim 4 wherein the bottom material layer is attached to the top material layer at the first and second end regions of each of the respective layers.

6. The apparatus of claim 4 wherein the width of the top material layer is less than the width of the bottom material layer.

7. The apparatus of claim 4 wherein the length of the top material layer is less than the length of the bottom material layer.

8. The apparatus of claim 4 wherein the thickness of the top material layer is less than the thickness of the bottom material layer.

9. The apparatus of claim 2 wherein the top portion, the bottom portion, or both top and bottom portions of the compressible pad comprises a fabric, a skinned foam, an open-cell foam, a closed-cell foam, a woven or nonwoven fabric, a woven or nonwoven mesh, a natural or synthetic leather, or a low density silicone.

10. The apparatus of claim 2 wherein the top portion and the bottom portion are made of different materials than each other.

11. The apparatus of claim 2 wherein the compressible pad comprises one or more openings in both the top portion and bottom portion that are configured to align with one or more openings in the headband when the apparatus is worn, wherein the one or more openings in the top portion are a different size from the one or more openings in the bottom portion.

12. The apparatus of claim 11 wherein the number of openings defined through the compressible pad when the top portion and bottom portion are attached to each other is different from the number of openings in the headband.

13. The apparatus of claim 2 further comprising an attachment device fastening the top portion to the bottom portion, wherein the device includes an insert having one end with a mushroom-cap type shape.

14. The apparatus of claim 1 wherein the compressible pad spans at least a portion of each of the one or more openings in the headband.

15. The apparatus of claim 1 wherein the bottom surface of the compressible pad extends at least 5 mm below the bottom side of the headband.

16. The apparatus of claim 1 further comprising
    a processor, configured to receive an incoming signal and create an output signal; and a speaker disposed on the apparatus, the speaker configured to produce the output from the processor.

17. The apparatus of claim 16 further comprising a microphone disposed on the apparatus, the microphone configured to pick up an input sound wave from the environment and convert the input sound wave to an incoming signal.

18. An apparatus for hearing protection, comprising:
    first and second ear cups, each ear cup defining a cavity configured to fit a user's ear;
    a headband having a first end affixed to a first ear cup and a second end affixed to a second ear cup, the headband having a central line from the first end to the second end and the headband also having a front side, a back side, a top side, a bottom side, and a thickness, the headband defining one or more openings along the central line that span the thickness of the headband from the top side to the bottom side; and
    a removable compressible pad spanning at least a portion of the one or more openings, the removable compressible pad having a top surface, a bottom surface, and an attachment region comprising a channel or groove wherein the attachment region is disposed between the top surface and bottom surface, wherein the channel or grove is configured to position at least a portion of the compressible pad inside the one or more openings so that the bottom surface of the compressible pad contacts the head of a user when the apparatus is worn, and wherein the compressible pad comprises one or more openings that are configured to align with one or more openings in the headband when the apparatus is worn.

* * * * *